US00PP15726P2

(12) United States Plant Patent
Dümmen

(10) Patent No.: US PP15,726 P2
(45) Date of Patent: Apr. 19, 2005

(54) ***GERANIUM* PLANT NAMED 'DUEIMGABRI'**

(50) Latin Name: *Pelargonium×hortorum*
Varietal Denomination: Dueimgabri

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/859,497

(22) Filed: Jun. 1, 2004

(30) Foreign Application Priority Data

Apr. 23, 2001 (QZ) ..... PBR 20019999

(51) Int. Cl.[7] ..... A01H 5/00
(52) U.S. Cl. ..... Plt./327

(58) Field of Search ..... Plt./327

(56) References Cited

PUBLICATIONS

UPOV–ROM GTITM Computer Database 2004/04, GTI Jouve Retrieval Software, Citation for 'Dueimgabri'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Zonal *Geranium* plant named 'Dueimgabri', characterized by its upright, somewhat outwardly spreading and rounded plant habit; freely branching habit; foliage with distinct zonation pattern; freely and early flowering habit; and dark pink-colored semi-double flowers.

1 Drawing Sheet

Botanical classification/cultivar denomination: *Pelargonium×hortorum* cultivar Dueimgabri.

BACKGROUND OF THE INVENTION

The present invention relates to a new and distinct cultivar of Zonal *Geranium* plant, botanically known as *Pelargonium×hortorum,* and hereinafter referred to by the name 'Dueimgabri'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor in May, 1998, of a proprietary selection of *Pelargonium peltatum* identified as code number N-02-05, not patented, as the female, or seed, parent with a proprietary selection of *Pelargonium peltatum* identified as code number E-12-250, not patented, as the male, or pollen, parent. The cultivar Dueimgabri was discovered and selected by the Inventor as a flowering plant within the progeny from this cross-pollination in a controlled environment in Rheinberg, Germany in April, 2001.

Asexual reproduction of the new cultivar by terminal vegetative cuttings at Rheinberg, Germany since July, 2001, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Dueimgabri'. These characteristics in combination distinguish 'Dueimgabri' as a new cultivar and distinguish it from other known Zonal *Geranium* cultivars:

1. Upright, somewhat outwardly spreading and rounded plant habit.

2. Freely branching habit.
3. Foliage with distinct zonation pattern.
4. Freely and early flowering habit.
5. Dark pink-colored semi-double flowers.

Compared to plants of the parent selections, plants of the new Zonal *Geranium* differ in flower coloration.

The new Zonal *Geranium* can be compared to plants of the cultivar HWD Gabrieli, disclosed in U.S. Plant Pat. No. 9,745. In side-by-side comparisons conducted in Rheinberg, Germany, plants of the new Zonal *Geranium* differed from plants of the cultivar HWD Gabrieli in the following characteristics:

1. Plants of the new Zonal *Geranium* had slightly smaller flowers than plants of the cultivar HWD Gabrieli.
2. Flowers of plants of the new Zonal *Geranium* were darker in color than flowers of plants of the cultivar HWD Gabrieli.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Dueimgabri' grown in a container.

DETAILED BOTANICAL DESCRIPTION

The cultivar Dueimgabri has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium×hortorum* cultivar Dueimgabri.

Parentage:

*Female parent.*—Proprietary selection of *Pelargonium×hortorum* identified as N-02-05, not patented.

*Male parent.*—Proprietary selection of *Pelargonium×hortorum* identified as E-12-250, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Moderately vigorous. Freely branching, about eleven lateral branches per plant.

*Plant height.*—About 37 cm.

*Plant width.*—About 21 cm.

*Lateral branches.*—Length: About 25.8 cm. Internode length: About 4.7 cm. Texture: Smooth. Color: 144A.

*Foliage description.*—Arrangement: Alternate, single. Length: About 5.9 cm. Width: About 9.4 cm. Shape: Reniform. Apex: Rounded. Base: Cordate. Margin: Crenate. Venation pattern: Palmate. Texture, upper and lower surfaces: Pubescent. Color: Developing foliage, upper surface: 137C. Developing foliage, lower surface: 138B. Fully expanded foliage, upper surface: 137A. Fully expanded foliage, lower surface: 137C. Venation, upper and lower surfaces: 144A. Zonation pattern: Distinct. Width: About 1.9 cm. Color: 147A. Petiole: Length: About 5.9 cm. Diameter: About 2.6 mm. Color, upper and lower surfaces: 144A.

Flower description:

*Flower arrangement.*—Dark pink-colored semi-double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about eleven open umbels with about 25 flowers per umbel.

*Flowering season.*—Flowering continuous spring until the autumn. Plants begin flowering about six weeks after planting.

*Flower longevity.*—Flowers last about five to seven days on the plant.

*Umbel size.*—Diameter: About 9.7 cm. Height: About 8.5 cm.

*Flower size.*—Diameter: About 4 cm. Depth (height): About 2 cm.

*Flower buds.*—Length: About 11.6 mm. Diameter: About 7.3 mm. Shape: Ovoid. Color: 144A.

*Petals.*—Quantity per flower: About five or six. Length: About 2.2 cm. Width: About 1.9 cm. Shape: Obovate. Apex: Rounded. Base: Attenuate. Margin: Entire; sinuate. Texture, upper and lower surfaces: Smooth. Color: When opening, upper surface: 41B; towards the base and margin, close to 155D. When opening, lower surface: 41C to 41D; towards the base and margin, close to 155D. Fully opened, upper surface: 41B to 41C; towards the base and margin, close to 155D; color becoming closer to 43C to 43D with development. Fully opened, lower surface: 41D; towards the base and margin, close to 155D.

*Petaloids.*—Quantity per flower: About three or four. Length: About 1.9 cm. Width: About 1.3 cm. Shape: Obovate. Apex: Rounded. Base: Attenuate. Margin: Entire; sinuate. Texture, upper and lower surfaces: Smooth. Color: When opening, upper surface: 41B; towards the base and margin, close to 155D. When opening, lower surface: 41C to 41D; towards the base and margin, close to 155D. Fully opened, upper surface: 41B to 41C; towards the base and margin, close to 155D; color becoming closer to 43C to 43D with development. Fully opened, lower surface: 41D; towards the base and margin, close to 155D.

*Sepals.*—Quantity per flower: About five or six, arranged in a single whorl. Length: About 1 cm. Width: About 2.9 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 1.9 cm. Diameter: About 2 cm. Angle: Mostly erect. Strength: Moderately strong. Texture: Smooth; glabrous. Color: 144A.

*Pedicel* (*individual flower stem*).—Length: About 2.1 cm. Diameter: About 7.5 mm. Angle: Mostly erect. Strength: Moderately strong. Texture: Pubescent. Color: 144A overlain with 178A.

*Reproductive organs.*—Androecium: Anther quantity per flower: About five to seven. Anther length: About 3 mm. Anther shape: Ovate. Anther color: 52B. Pollen amount: Moderate. Pollen color: 28A. Gynoecium: Pistil quantity per flower: One. Pistil length: About 9.2 mm. Stigma shape: Five-parted, star-shaped. Stigma color: 61B. Style length: About 4.7 mm. Style color: 144B. Ovary color: 144A.

*Seed/fruit.*—Development of seeds and fruit have not been observed.

Disease/pest resistance: Plants of the new Zonal *Geranium* have not been observed to be resistant to pathogens and pests common to Zonal *Geraniums*.

Temperature tolerance: Plants of the new Zonal *Geranium* have been observed to be tolerant to temperatures ranging from 5 to 40° C.

It is claimed:

1. A new and distinct cultivar of Zonal *Geranium* plant named 'Dueimgabri', as herein illustrated and described.

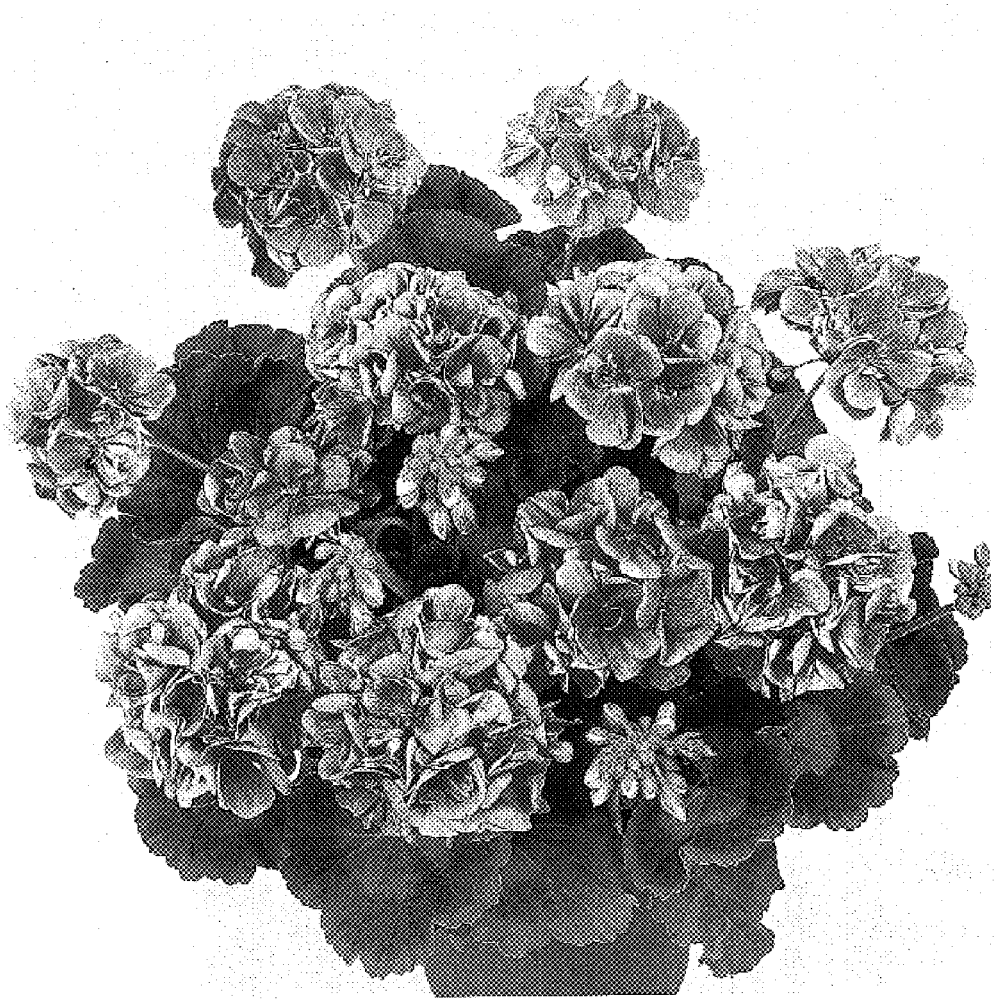

* * * * *